(12) United States Patent
Amtmann et al.

(10) Patent No.: US 6,444,706 B2
(45) Date of Patent: Sep. 3, 2002

(54) GUANIDINE DERIVATIVES, PROCESSES FOR PREPARING THEM AND THEIR USE AS PHARMACEUTICAL COMPOSITIONS

(75) Inventors: Eberhard Amtmann; Norbert Frank; Gerhard Sauer, all of Heidelberg; Gerhard Schilling, Ladenburg, all of (DE)

(73) Assignee: Cancer Research Ventures Limited, London (GB)

(*) Notice: Subject to any disclaimer, the term of this patent is extended or adjusted under 35 U.S.C. 154(b) by 0 days.

(21) Appl. No.: 09/815,995

(22) Filed: Mar. 23, 2001

Related U.S. Application Data

(62) Division of application No. 09/194,321, filed as application No. PCT/EP97/02658 on May 23, 1997, now Pat. No. 6,284,798.

(30) Foreign Application Priority Data

May 24, 1996 (DE) .......................... 196 21 038

(51) Int. Cl.⁷ .................. A61K 31/15; A61K 31/155
(52) U.S. Cl. .................. 514/631; 514/632; 514/634; 514/635; 514/637; 514/2; 514/8
(58) Field of Search ................ 514/2, 8, 631, 514/632, 634, 635, 637

(56) References Cited

U.S. PATENT DOCUMENTS

| | | | |
|---|---|---|---|
| 3,914,308 A | 10/1975 | McCoy et al. | |
| 4,709,094 A | 11/1987 | Weber et al. | |
| 5,093,525 A | * 3/1992 | Weber et al. | ................ 564/238 |

FOREIGN PATENT DOCUMENTS

| | | |
|---|---|---|
| GB | 932951 | 7/1963 |
| WO | US90 02398 | 5/1990 |
| WO | US91 01447 | 3/1991 |
| WO | US91 06030 | 8/1991 |
| WO | US92 01050 | 2/1992 |

OTHER PUBLICATIONS

CA:87:23199 abs of Probl. Farm. by Gagauzov et al, 3, pp. 51–6.
CA:88:111391 abs of J Mol Biol by Sanchez et al 30 (2) pp. 223–53.
Z. Jerushalmy, et al. Inhibition by Guanidino Compounds of Platelet Aggregation Induced By Adenosine Diphosphate. *Biochemical Pharmacology* (1966) 15:1791–1803.
Krishna C. Agrawal, et al. Potential Antitumor Agents. II. Effects of Modifications in the Side Chain of 1–Formylisoquinoline Thiosemicarbazone[1,2]. *J. Med. Chem.* (1969) 12,5:771–774.
Barnett S. Pitzele, et al. Potential Antisecretory Antidiarrheals. 1. $\beta_2$–Adrenergic Aromatic Aminoguanidine Hydrazones. *J. Med. Chem.* (1988) 31:138–144.
Raj Nandan Prasad, et al. Acylation of guanidines and guanylhydrazones. *Canadian Journal of Chemistry.* (1967) 45:2247–2252.
William O. Foye, et al. Synthesis and Biological Activity of Guanylhydrazones of 2–and–4–Pyridne and 4–Guinoline Carboxaldehydes. *Journal of Pharmaceutical Sciences* (Jun. 1990) 79,6:527–530.
Basil Jason Heywood, et al. Improvements in or relating to Guanidines. Patent Specification No. 932951 –The Patent Office–London. Published 7/31/63.
Chemical Abstracts. (1975) vol. 83, 53182:16.

\* cited by examiner

*Primary Examiner*—Frederick Krass
(74) *Attorney, Agent, or Firm*—Dann Dorfman Herrell and Skillman, P.C.

(57) ABSTRACT

The invention concerns new guanidine derivatives of formula (I), methods of preparing them and their use in drugs containing such compounds.

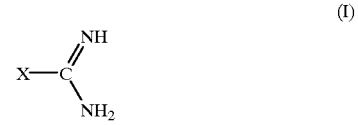

(I)

10 Claims, 7 Drawing Sheets

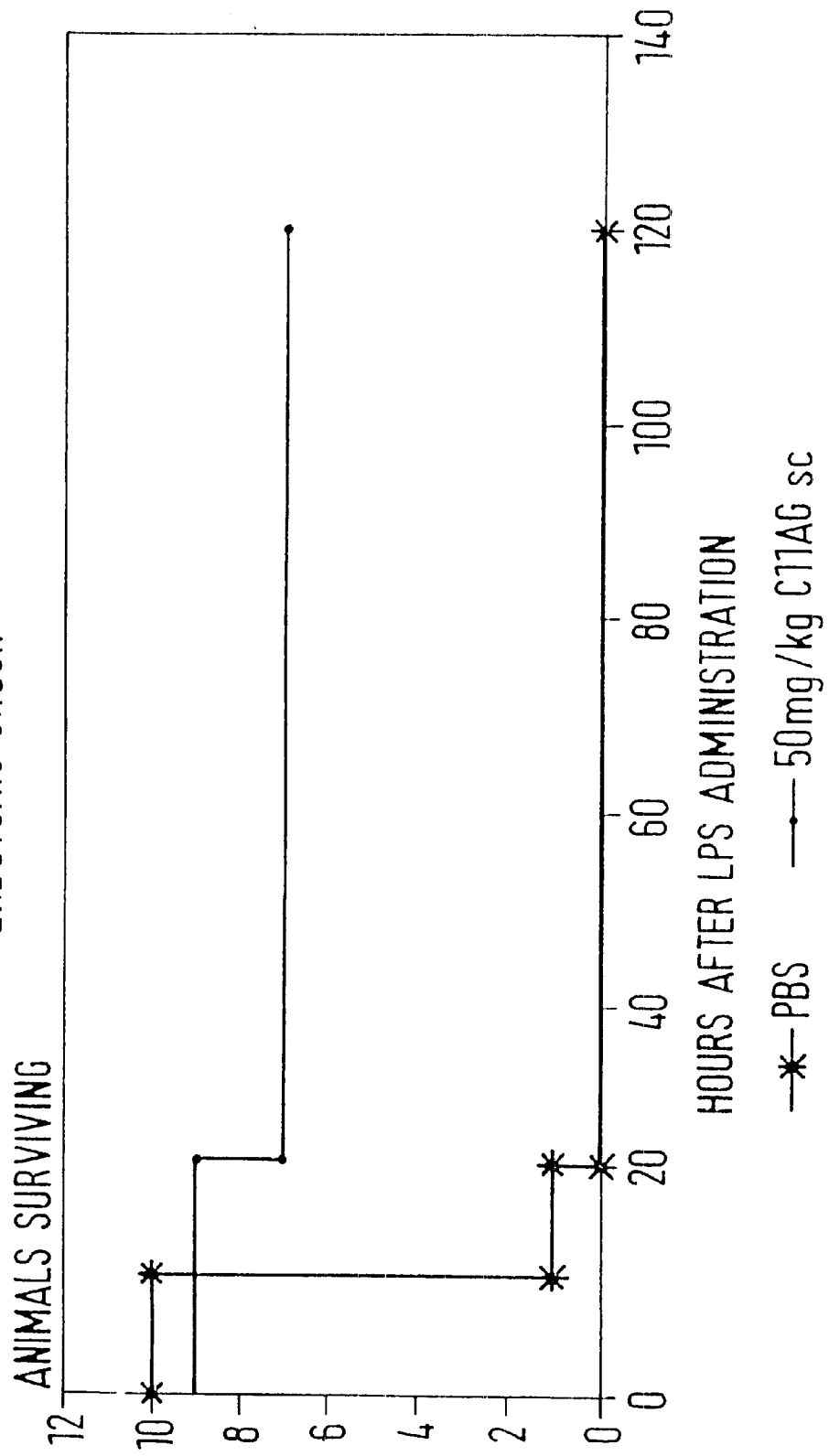

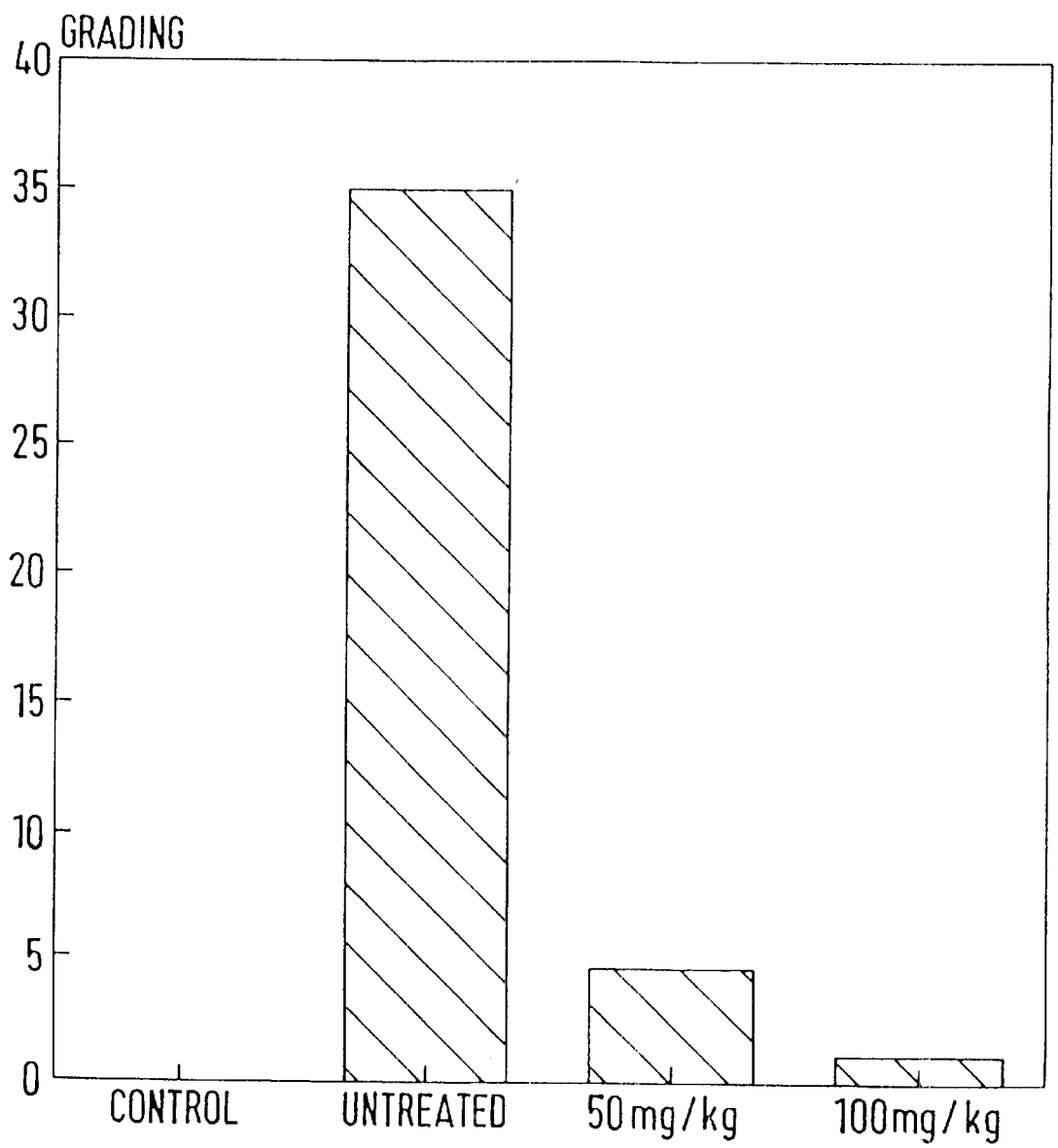

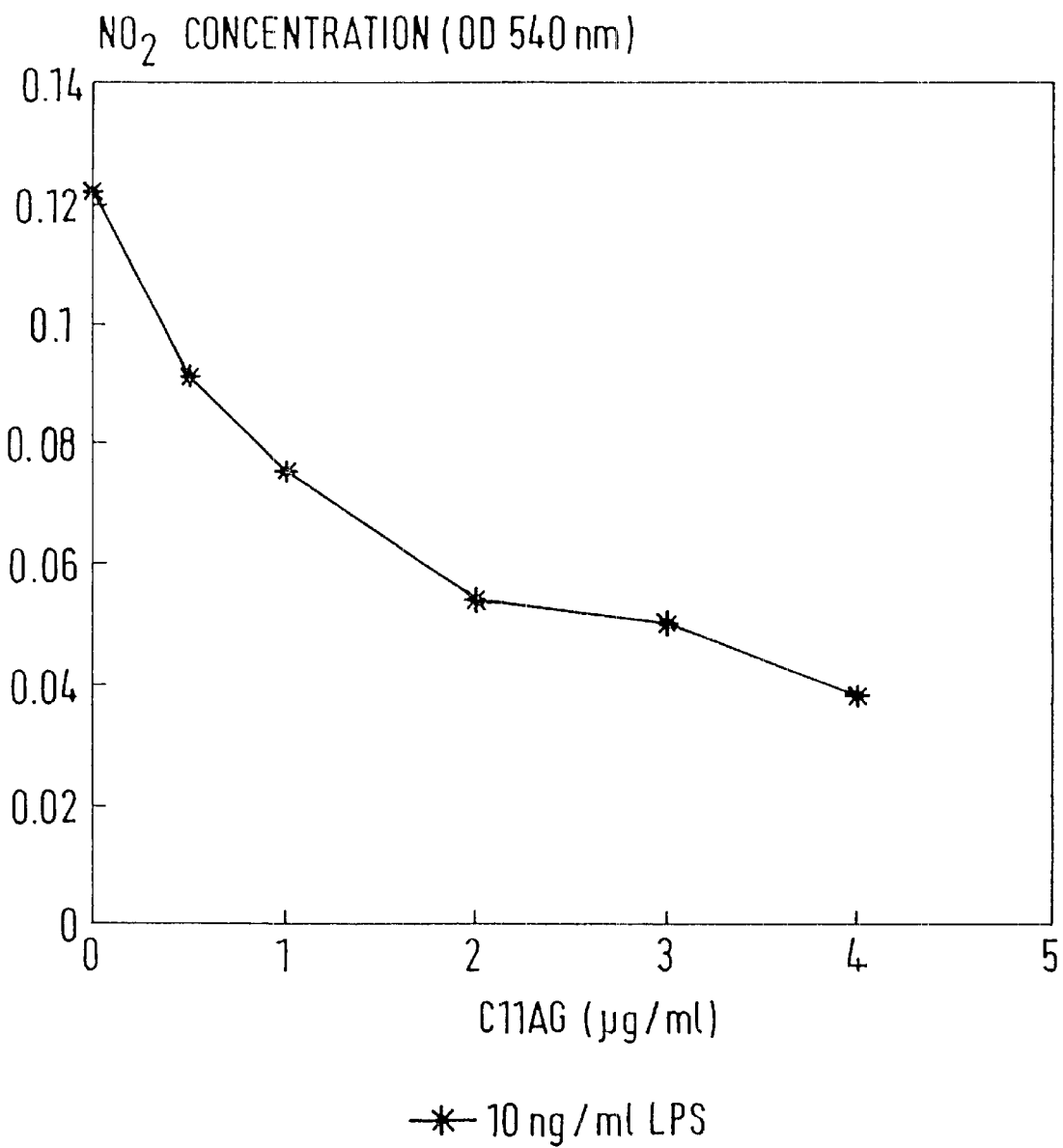

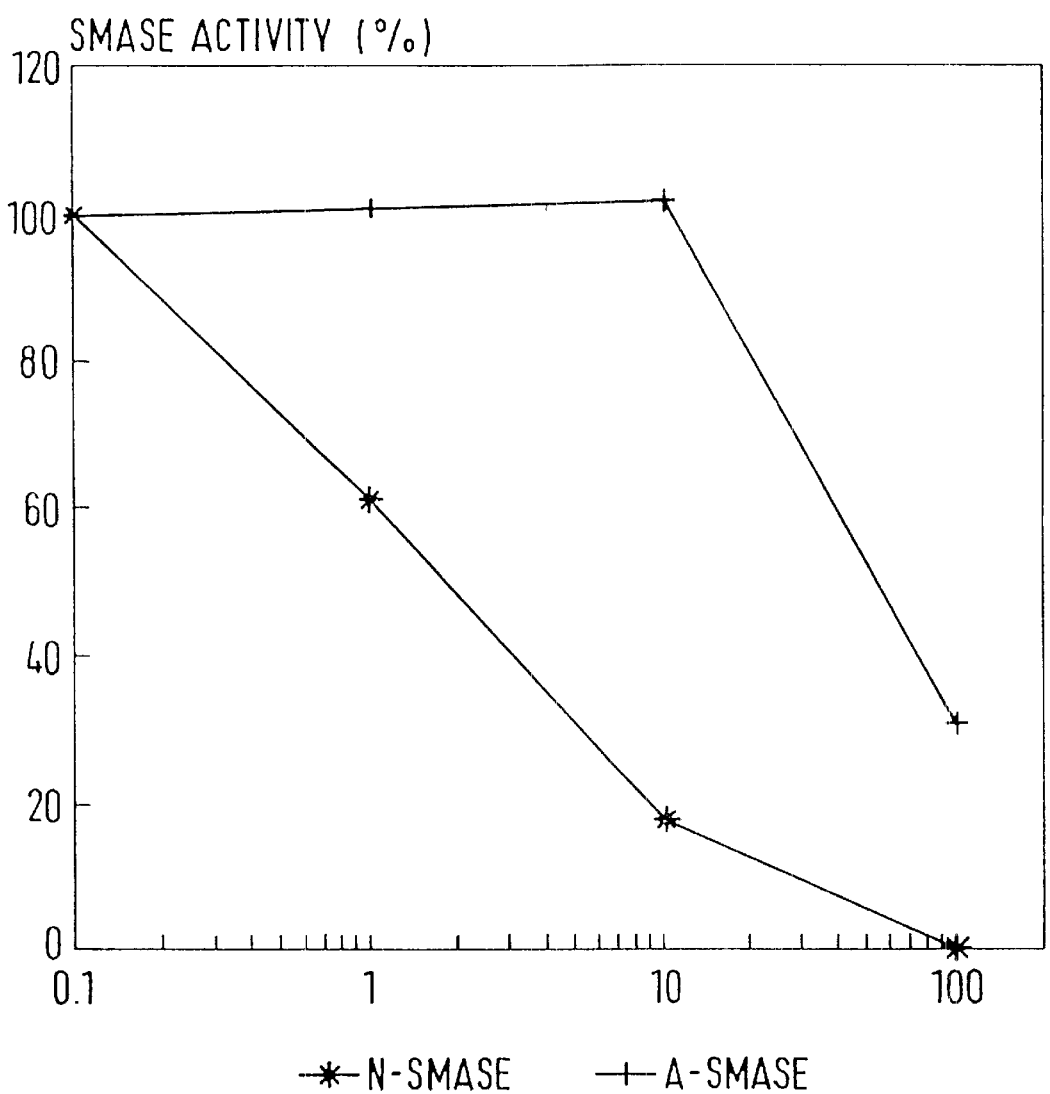

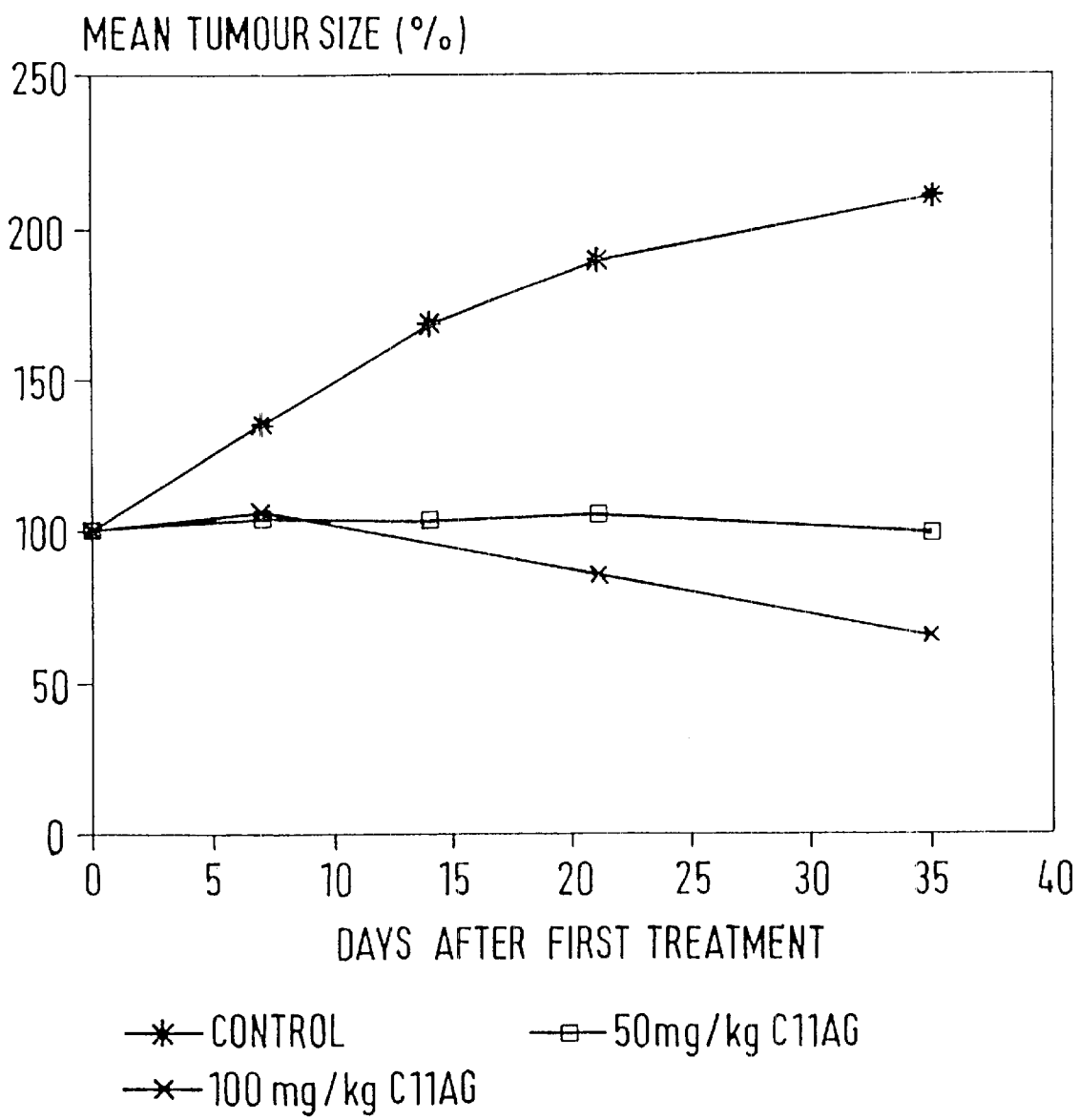

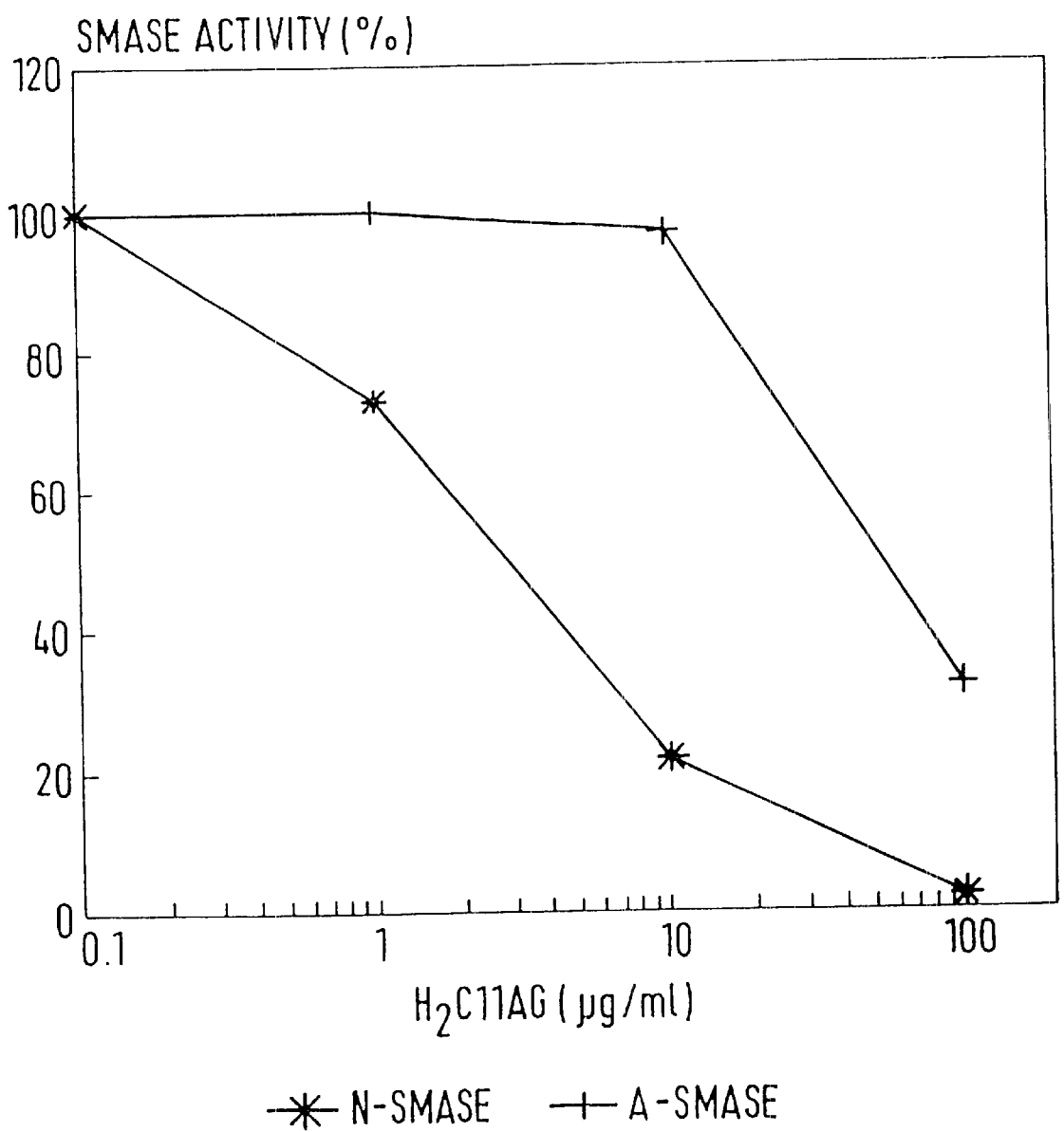

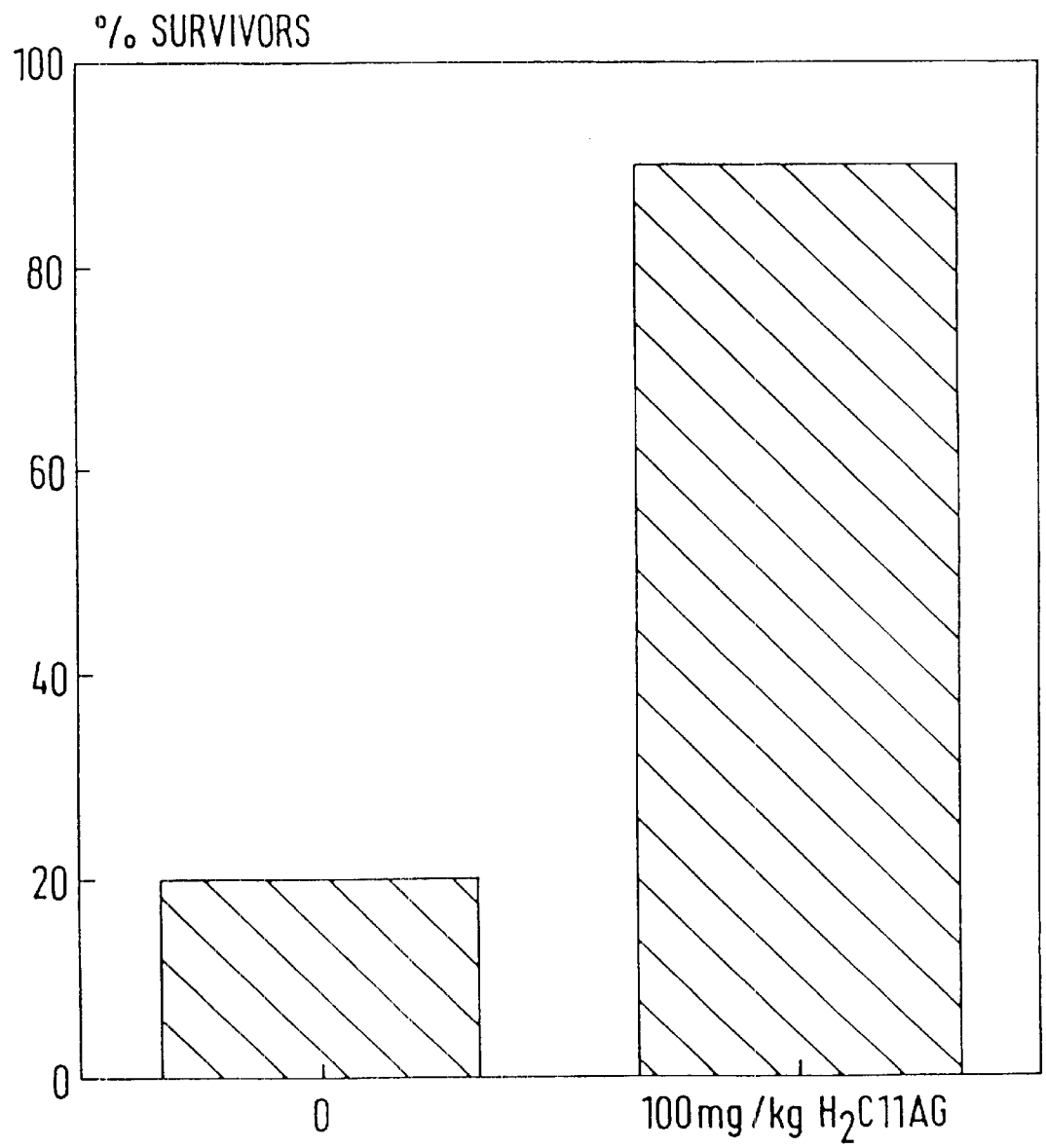

GUANIDINE DERIVATIVES, PROCESSES FOR PREPARING THEM AND THEIR USE AS PHARMACEUTICAL COMPOSITIONS

This application is a divisional of U.S. application Ser. No. 09/194,321, filed Oct. 18, 1999, now U.S. Pat. No. 6,284,798 which was the National Stage of International Application No. PCT/EP97/02658, filed May 23, 1997. The disclosures of the aforesaid applications are incorporated by reference in their entireties into the present application.

The present invention relates to new guanidine derivatives, processes for preparing them and their use as sphingomyelinase inhibitors and pharmaceutical compositions which contain these compounds.

The guanidine derivatives of the present invention correspond to the general formula I:

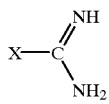

wherein

X denotes $R_1$, —$NHR_1$, —NH—NH—$CHR_1R_2$, —NH—N=$CR_1R_2$,

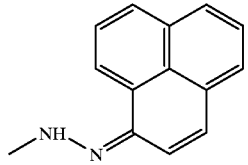

$R_1$ and $R_2$ independently of each other denote hydrogen, a straight-chained or branched $C_{3-20}$-alkyl, $C_{3-20}$-cycloalkyl group, an adamantyl, norbornyl, tricyclodecyl, benzyl, furyl, pyridyl, indolyl, quinolyl, anthracenyl, phenanthryl, perinaphthyl or quinuclidinyl group, wherein the above-mentioned straight-chained or branched $C_{3-20}$-alkyl group may be substituted by a hydroxy or $C_{1-4}$-alkoxy group, a halogen atom or an amino group and the above-mentioned $C_{3-20}$-cycloalkyl group may be substituted by a hydroxy, $C_{1-4}$-alkoxy, $C_{1-4}$-alkyl group or by a halogen atom or an amino group, and wherein, if X denotes —NH—N=$CR_1$ $R_2$, only one of the substituents $R_1$ and $R_2$ may represent hydrogen optionally in the form of individual optical isomers, mixtures of the individual isomers or racemates, tautomers or geometrical isomers e.g. cis/trans-isomers as well as in the form of the free bases or the corresponding acid addition salts with pharmacologically acceptable acids.

Preferred compounds of general formula I are those wherein

X denotes —NH—NH—$CH_2R_1$ and —NH—N=$CHR_1$ $R_1$ denotes $C_{8-20}$-alkyl (branched or unbranched).

Particularly preferred compounds of general formula I are those wherein

X denotes —NH—NH—$CH_2R_1$ and —NH—N=$CHR_1$ and $R_1$ denotes an unbranched decyl group.

The compounds according to the invention have valuable pharmacodynamic and biochemical properties and can therefore be used advantageously in research and in human and veterinary medicine.

Surprisingly it has been found that the aminoguanidines and amidines according to the invention have beneficial sphingomyelinase-inhibiting, antimicrobial, antiviral, anti-inflammatory (e.g. anti-shock) activities and effects on cell growth.

The compounds according to the invention are prepared by reacting an aldehyde or ketone of formula $R_1CHO$ or $R_1COR_2$ with aminoguanidine. The reaction is usually carried out in an inert organic solvent, e.g. a chlorinated hydrocarbon, such as dichloromethane or chloroform, or an aromatic hydrocarbon such as benzene or toluene. The reaction is preferably carried out by removing the water formed from the equilibrium, e.g. using a water separator. The reaction may be carried out over a wide temperature range but is generally performed at elevated temperature, particularly at a temperature in the range from about 60° C. up to the boiling point of the reaction mixture. In addition, the compounds according to the invention may be prepared by methods known from the prior art.

The starting compounds are known or may be prepared by known methods.

The pharmaceutical compositions according to the invention contain one of the above-mentioned compounds of general formula I in a conventional solid or liquid pharmaceutical carrier. The compounds according to the invention may also be combined with known active substances.

The compounds according to the invention are characterised by anti-inflammatory (e.g. anti-shock), antimicrobial, antitumoral and, in particular, antiviral effects. The antiviral spectrum of activity includes, for example, herpes, vesicular stomatitis, HIV and papilloma viruses. It has also been found that the compounds according to the invention influence the growth of tumour cells. They may be used to treat carcinomas, e.g. carcinoma of the large intestine, sarcomas or leukaemias.

In general, it is found that these substances according to the invention bring about an NF-kappaB-dependent immunosuppression.

The compounds according to the invention can therefore be used to treat the following diseases:

A. Systemic inflammatory reactions
   sepsis-causing diseases
      gram-positive sepsis
      gram-negative sepsis
      fungal sepsis
      agranulocytosis (neutropenic fever)
      urinary infections (urosepsis)
      general infections with meningococci (meningococcaemia)
   trauma/haemorrhage
   burns
   injuries caused by ionising radiation
   acute pancreatitis
   adult respiratory distress syndrome (ARDS)
B. Reperfusion syndrome
   post pump syndrome
   ischaemia-induced reperfusion injury
C. Cardiovascular disease:
   cardiac stun syndrome
   myocardial infarction
   congestive heart failure
   arteriosclerosis
D. Infectious diseases:
   papilloma virus infection
   herpes virus infection HIV infection/HIV neuropathy
meningitis
hepatitis
septic arthritis
peritonitis
pneumonia
bronchitis
epiglottitis
E. coli 0157:H7 infection
haemolytic uremic syndrome/thrombolytic thromocytopenic purpura
malaria
Dengue haemorrhagic fever
Leishmaniasis
leprosy
toxic shock syndrome
Streptococcal myositis
gas gangrene
myobacterium tuberculosis infections
myobacterium avium intracellular infections
pneumocystosis
pelvic inflammatory disease
orchitis/epidydimitis
Legionella
lyme disease
influenza A virus infection
diseases caused by Epstein-Barr virus
viral-associated haemaphagocytic syndrome
viral encephalitis/aseptic meningitis
E. Gynaecological applications
  premature labour
  miscarriage
  infertility
F. Inflammatory diseases/autoimmune diseases:
  rheumatoid arthritis/seronegative arthropathy
  emphysema bronchitis (chronic obstructive pulmonary disease COPD)
  osteoarthritis
  inflammatory bowel disease
  Crohn's disease
  systemic lupus erythematosis
  iridocyclitis/uveitis/optic neuritis
  idiopathic pulmonary fibrosis
  systemic vasculitis/Wegner's granulomatosis
  sarcoidosis
  orchitis/vasectomy reversal procedures
H. Allergic/atopic diseases:
  asthma
  allergic rhinitis
  eczema
  allergic contact dermatitis
  allergic conjunctivitis
  hypersensitive pneumonitis
I. Malignant disease:
  tumour therapy in combination with chemotherapy, radiotherapy and cytokine treatment such as TNF-α treatment of sarcomas, carcinomas and leukaemias
  ALL
  AML
  CML
  CLL
  breast cancer
  small-cell and non-small-cell bronchial carcinoma
  squamous cell carcinoma
  Hodgkin's disease, non-Hodgkin's lymphoma
  multiple melanoma
  Kaposi's sarcoma
  colorectal carcinoma
  nasopharyneal carcinoma
  malignant histiocytosis
  paraneoplastic syndrome/hypercalcaemia of malignancy
J. Transplant complications
  rejection reactions after transplant
  graft versus host reactions
K. Cachexia
L. Congenital diseases:
  cystic fibrosis
  familial hematophagocytic lymphohistiocytosis
  sickle cell anaemia
M. Skin diseases:
  psoriasis
  alopecia
N. Neurological diseases/chronic and acute neurodegeneration
  multiple sclerosis
  Parkinson's disease
  Down's syndrome
  stroke
  skull/brain trauma
  migraine
O. Diseases of the kidneys:
  nephrotic syndrome
  haemodialysis
  uraemia
P. Various toxicities:
  OKT3 therapy
  anti-CD3 therapy
  cytokine therapy
  chemotherapy
  radiation therapy
  chronic salicylate intoxication
Q. Metabolic/idiopathic diseases:
  Wilson's disease
  haemachromatosis
  alpha-1-antitrypsin deficiency
  diabetes
  Hashimoto's thyroiditis
  osteoporosis
  hypothalamic pituitary adrenal axis evaluation
  primary biliary cirrhosis In vitro investigations in plaque reduction tests using different viruses showed an inhibition of growth at substance concentrations of from 0.1 to 1000/µg/ml. The toxicity of the substances according to the invention is relatively low. They may be used in particular as effective preventative or therapeutic agents against influenza, AIDS or herpes diseases of the skin and mucous membranes. The daily dose for adults during the disease is of the order of about 5 to 1000 mg of active substance per day.

The compounds according to the invention may be administered by parental, subcutaneous, intravenous, intramuscular and intraperitoneal route. In this case, the carrier substance is a sterile liquid such as water or oil, the oil being of vegetable, animal or synthetic origin. Conventional glucose solutions are used as the injectable solutions. The liquid carriers for the injectable solutions generally contain 0.5 to 26% by weight of active substance. The compounds according to the invention may be administered orally with equal success. The compounds are also suitable for treating pneumonia and are administered in the form of a vapour or spray to the oral and nasal cavity. For oral administration, compositions in the form of tablets, capsules, powders, solutions, suspensions or elixirs are particularly preferred. The quantity of active ingredient in these preparations is at least 1% by weight, based on the total weight of the composition. The active substances according to the invention may also be administered topically, e.g. in ointments, creams, emulsions or lotions.

The Examples which follow show some possible formulations for the preparations:

BRIEF DESCRIPTION OF THE DRAWINGS

FIG. 1 illustrates the effect of C11AG on endotoxic shock.

FIG. 2 illustrates the effect of C11AG booster injection.

FIG. 3 illustrates the effect of C11AG on NO-synthase induction.

FIG. 4 illustrates the effect of C11AG on sphingomyelinase.

FIG. 5 illustrates the effect of C11AG on tumors.

FIG. 6 illustrates the effect of C11AG on neutral sphingomyelinase.

FIG. 7 illustrates the effect of C11AG on survival rate.

FORMULATION EXAMPLES

1. Tablets
Composition:

| Active substance according to the invention | 20 parts by weight |
|---|---|
| Stearic acid | 6 parts by weight |
| Glucose | 474 parts by weight |

The ingredients are processed in the usual way to form tablets weighing 500 mg. If desired, the content of active substance may be increased or reduced and the quantity of glucose reduced or increased accordingly.

2. Suppositories
Composition:

| Active substance according to the invention | 100 parts by weight |
|---|---|
| Powdered lactose | 45 parts by weight |
| Cocoa butter | 1555 parts by weight |

The ingredients are processed in the usual way to form suppositories weighing 1.7 g.

3. Powder for Inhalation

Micronised powdered active substance (compound of formula I; particle size about 0.5 to 7 μm) is packed into hard gelatine capsules in a quantity of 5 mg, optionally with the addition of micronised lactose. The powder is inhaled from conventional inhalers, e.g. according to DE-A 33 45 722, to which reference is hereby made.

The compounds according to the invention can be prepared starting from compounds known from the prior art, using the processes described in the following Examples, inter alia. Other different embodiments of the invention and processes will be apparent to anyone skilled in the art from the present specification. However, it is expressly pointed out that these Examples and the associated specification are intended solely for purposes of explanation and should not be regarded as restricting the invention. Reference is further made to German Patent Application P 196 21 038.0 for additional information.

Example 1

Preparation of 1-(undecylideneamino)guanidine [C11AG]

1 mol (170.3 g) of undecanal, 1.1 mol (150 g) of aminoguanidine hydrogen carbonate and 1 g of p-toluenesulphonic acid are mixed with 500 ml of toluene and refluxed with stirring. As soon as 2 mol of water have been separated using the water separator, the mixture is allowed to cool, concentrated by rotary evaporation and the dark red oil is taken up in 250 ml of petroleum ether 40/60°. The precipitate formed is filtered and washed again with petroleum ether. For recrystallisation the precipitate is dissolved in ethyl acetate and mixed with petroleum ether at boiling temperature (boiling range 40 to 60° C.) until beginning to turn cloudy. Fine crystals are obtained, m.p. 101° C. The structure and purity of the compound were confirmed by analytical and spectroscopic data.

The other compounds mentioned in Example 3 are prepared analogously.

Example 2

Preparation of 1-(undecylamino) guanidine [$H_2$C11AG]

1.2 g of 1-(undecylideneamino)guanidine are placed in an autoclave and hydrogenated over a period of 12 hours in the presence of 0.1 g of 10% palladium on activated charcoal as hydrogenation catalyst in 20 ml of 100% acetic acid under a hydrogen pressure of 60 bar at ambient temperature. Then the catalyst is filtered off and the colourless solution is evaporated to dryness in vacuo.

In this way the title compound is isolated, after recrystallisation from ethyl acetate, in the form of colourless crystals melting in the range from 70–72° C. in quantitative yield.

Example 3

The virostatic properties were determined by in vitro tests. The following virus strains were used:

herpes virus
vesicular stomatitis virus
BVI 1

Cell cultures (monkey kidney cells or human fibroblasts) are infected with herpes and a series of cultures are exposed to medium containing various concentrations of the test substance. After 24 hours the concentration of the virus descendants in the cell culture supernatant is determined by plaque assays. The concentration of substance at which the virus replication is inhibited by 50% ($IC_{50}$) is determined from dosage/activity curves.

The results obtained from some substances by way of example are listed in the following Table.

| Substance | IC$_{50}$ µM |
| --- | --- |
| 1-(octylidene-amino)guanidine | 49.7 |
| 1-(nonylidene-amino)guanidine | 29.0 |
| 1-(decylidene-amino)guanidine | 28.9 |
| 1-(undecylidene-amino)guanidine | 6.8 |
| 1-(dodecylideneamino)guanidine | 3.2 |
| 1-(anthracen-9-ylmethylene-amino)guanidine | 1.5 |
| 1-(indol-3-ylmethylene-amino)guanidine | 19.8 |
| 1-(phenalen-1-ylidene-amino)guanidine | 45.4 |

Example 4

Protection from endotoxic shock by C11AG is illustrated by FIG. 1:

Mice (strain NMRI/Nu, 8 weeks old, female) were each given 0.2 mg of endotoxin from *E. coli* (Sigma, Munich) by intraperitoneal route. The 10 control animals, who had been given 0.2 ml of 5% glucose subcutaneously, died within 24 hours. Nine animals were injected subcutaneously with 50 mg/kg of C11AG 30 minutes before the endotoxin treatment. Of this group, only 2 animals died.

Example 5

Inhibition of collagen-induced arthritis in the mouse.

An autoimmune reaction against cartilagenous tissue was produced by injecting collagen into DBA/I mice as described (Holmdahl, R. et al., Immunology, 65, 305–310, 1988). Groups of 10 animals were used as control or were given 50 mg/kg or 100 mg/kg of C11AG per day by oral route. The drug was administered in the food (Altromin, powdered food) and the dosage was calculated from the daily food intake. The symptoms were evaluated daily for each individual paw from 0.5–3 as described [R. Holmdahl, et al., Immunology, 65, 305–310, (1988)]. The total symptoms of every animal in each group—on day 7 after the booster injection—are shown in the following Table:

| Treatment | Total Symptoms |
| --- | --- |
| Control | 0 |
| Collagen | 35 |
| Collagen/50 mg/kg C11AG | 4.5 |
| Collagen/100 mg/kg C11AG | 1 |

20 days after the booster injection the animals were killed and the joints were examined by histopathology resulting in the following picture:

In all the untreated animals, inflammatory processes were found, but in the animals and controls treated with 50 and 100 mg/kg of C11AG, no such inflammatory processes could be detected.

The results obtained seven days after the booster injection are graphically shown in FIG. 2.

Example 6

| Inhibition of neutral SMase | |
| --- | --- |
| Compound | Neutral SMase IC$_{50}$ [µM] |
| Octylidene-aminoguanidine | 63 |
| Decylidene-aminoguanidine | 44 |
| Undecylidene-aminoguanidine | 8.2 |
| Dodecylidene-aminoguanidine | 5.8 |
| Anthracen-9-ylmethylene-aminoguanidine | 1.9 |
| Indol-3-ylmethylene-aminoguanidine | 5 |
| Phenalen-1-ylidene-aminoguanidine | 54 |

$^{14}$C sphingomyelin (10 µg/ml) was incubated with neutral SMase (membrane fraction isolated from mice brains, 10 µg of protein/mixture [according to S. Gatt, Biochem. Biophys. Res. Commun. 68, 235–241 (1976)] in the presence of various concentrations of the test substances (for 2 hours at 37° C. 20 mM Tris, 1 mM MgCl$_2$.pH 7.5). Then the samples were extracted with 5 times the volume of chloroform/methanol (1:1) and the content of radioactive phosphorylcholine in the aqueous phase was determined. The IC$_{50}$ was obtained from dosage/activity curves.

Example 7

Inhibition of NO-aynthase induction by C11AG in macrophages.

RAW cells (mouse macrophage line, origin: American Type Culture Collection) were treated with 10 ng/ml of endotoxin from *E. coli* (LPS) in the presence of different concentrations of C11AG. After 16 hours the nitrite content in the culture medium was measured using the method described [K. Tschaikowsky, M. Meisner, F. Schonhuber and E. Rugheimer, Br. J. Pharmacol. 113 (3): 664–8 (1994)]. Measured Values:

| C11AG concentration [µg/ml] | OD 540 nm |
| --- | --- |
| 0 | 0.122 |
| 0.5 | 0.091 |
| 1 | 0.075 |
| 2 | 0.054 |
| 3 | 0.05 |
| 4 | 0.038 |

The inhibition of NO-synthase induction is graphically shown in FIG. 3; the NO$_2$ concentration [OD measured at 540 nm] is plotted against the C11AG concentration [µg/ml] for 10 ng/ml of LPS.

Example 8

C11AG-IC$_{50}$ determination of acidic and neutral Smase.

$^{14}$C sphingomyelin (10 µg/ml) were incubated with neutral SMase (membrane fraction isolated from mouse brains, 10 µg protein/mixture, according to Gatt, S. Biochem. Biophys. Res. Commun. 68, 235–241, 1976) or with acidic SMase (microsome fraction from macrophage 5 µg of protein/mixture isolated according to Gatt, S. Biochem. Biophys. Res. Commun. 68, 235–241, 1976) in the presence of various concentrations of the test substances, for 2 hours at 37° C. in 20 mM Tris, 1 mM MgCl$_2$, pH 7.5 (neutral SMase) or in 50 mM sodium acetate, 1 mM MgCl$_2$, pH 5.6 (acid SMase). Then the samples were extracted with 5 times the volume of chloroform/methanol (1:1) and the content of radioactive phosphorylcholine in the aqueous phase was determined. The release of phosphorylcholine in the untreated mixtures corresponds to 100% enzyme activity.
Measured Values:

| C11AG concentration [μg/ml] | nSMase activity [%] | aSMase activity [%] |
|---|---|---|
| 0 | 100 | 100 |
| 1 | 61 | 101 |
| 10 | 18 | 102 |
| 100 | 0 | 31 |

FIG. 4 shows, by a simple logarithmic representation, the sphingomyelinase inhibition for neutral and acidic sphingomyelinase [in %] as a function of the C11AG concentration [μg/ml].

Example 9

Inhibition of the growth of papillomas.

*Mastomys natalensis* with papillomas triggered by a papilloma virus [see E. Amtmann and K. Wayss: ※ The *Mastomys natalensis* papilloma virus, in: P. Salzman and P. Howley (Eds.): The Papovaviridae, Vol. 2. Plenum Publishing Corporation (1987)] were given food containing various amounts of C11AG. The food consumption was measured and from this the daily oral dose of C11AG was calculated. The size of the papilloma was measured in two dimensions by means of a sliding gauge and the relative growth was calculated. 10 animals were treated per dose.

FIG. 5 graphically shows the average tumour size as a function of the duration of treatment for various doses of C11AG. Curve A shows the tumour growth of the control animals. Curve B shows the pattern of size for a dosage of 50 mg/kg C11AG and curve C shows the corresponding pattern for 100 mg/kg C11AG.

Example 10

Hydrogenated C11AG-IC$_{50}$: Measurement of acidic and neutral SMase.

$^{14}$C-sphingomyelin (10 μg/ml) was incubated with neutral SMase (membrane fraction from mouse brain, 10 μg of protein/batch, isolated according to Gatt, S. Biochem. Biophys. Res. Commun. 68, 235–241, 1976) or with acid SMase (microsome fraction from macrophages 5 μg of protein per batch [isolated according to S. Gatt, Biochem. Biophys. Res. Commun. 68, 235–241, (1976)] in the presence of various concentrations of the test substances for 2 hours at 37° C. in 20 mM Tris, 1 mM MgCl$_2$, pH 7.5 (neutral SMase) or in 50 mM sodium acetate, 1 mM MgCl$_2$, pH 5.6 (acidic SMase). Then the samples were extracted with 5 times the volume of chloroform/methanol (1:1) and the content of radioactive phosphorylcholine in the aqueous phase was determined. The release of phosphorylcholine in the untreated batches corresponds to 100%.
Measured Values:

| H$_2$C11AG concentration [μg/ml] | nSMase activity [%] | aSMase activity [%] |
|---|---|---|
| 0 | 100 | 100 |
| 1 | 73 | 100 |
| 10 | 22 | 97 |
| 100 | 2 | 32 |

FIG. 6 shows, by a simple logarithmic representation, the sphingomyelinase inhibition for neutral—curve A—and acidic sphingomyelinase [in %]—curve B—as a function of the H$_2$C11AG concentration [μg/ml].

Example 11

Prevention of lethal endotoxic shock in the mouse by H$_2$C11AG.

10 mice of the Balb C strain (about 8 weeks old) were given 0.7 mg of endotoxin from *E. coli* (in 0.2 ml of isotonic saline solution) by intraperitoneal injection. 10 animals were given 100 mg/kg of H$_2$C11AG (dissolved in twice distilled water) by oesphageal tube 2 hours before the LPS treatment. The control animals were given water. The surviving animals were observed for 12 days.

Results: control: 2 survivors (20%), 100 mg/kg H$_2$C11AG (hydrogenated C11AG): 9 survivors (90%).

FIG. 7 shows the survival rate of untreated experimental animals (A) compared with those who were treated with a dose of 100 mg H$_2$C11AG, as described above.

To illustrate the nomenclature used in the application, here are the structures of some of the compounds mentioned:

1-(Anthracen-9-ylmethylene-amino)guanidine

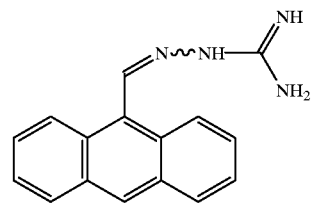

1-(Indol-3-ylmethylene-amino)guanidine

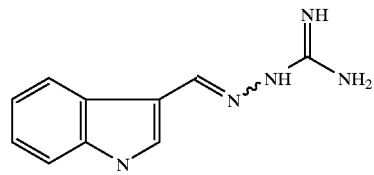

1-(Phenalen-1-ylidene-amino)guanidine

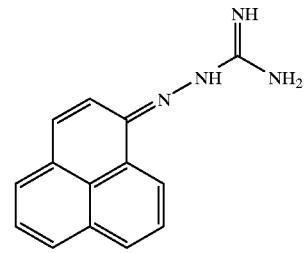

What is claimed is:

1. A method for treatment of a human or animal subject comprising administering to said subject an effective amount of a compound having the formula:

X—C(NH)NH$_2$ wherein X denotes —NH—NH—CH$_2$R$_1$ or —NH—N=CHR$_1$ and R$_1$ denotes C$_8$ to C$_{20}$-alkyl, either branched or unbranched, optionally in the form of the individual optical isomers, mixtures of the individual isomers or racemates, tautomers or the corresponding acid addition salts with pharmaceutically acceptable acids; wherein said treatment is for an inflammatory disease, autoimmune disease, cardiovascular disease, infectious disease, tumor therapy, or for inhibiting sphingomyelinase.

2. The method according to claim 1, wherein said treatment is for at least one inflammatory disease or autoimmune disease selected from the group consisting of rheumatoid arthritis, seronegative arthropathy, emphysema, bronchitis, chronic obstructure pulmonary disease (COPD), osteoarthritis, inflammatory bowel disease, Crohn's disease, systemic lupus erythematosis, iridocyclitis, uveitis, optic neuritis, idiopathic pulmonary fibrosis, systemic vasculitis/Wegner's granulomatosis, sarcoidosis and orchitis/vasectomy reversal procedures.

3. The method according to claim 1, wherein said treatment is for at least one cardiovascular disease selected from the group consisting of cardiac stun syndrome, myocardial infarction, congestive heart failure and arteriosclerosis.

4. The method according to claim 1, wherein said treatment is for at least one infectious disease selected from the group consisting of papilloma virus infectious, herpes virus infections, HIV infection/HIV neuropathology, meningitis, hepatitis, septic arthritis, peritonitis, pneumonia, bronchitis, epiglottitis, *E. coli* 0157:H7 infection, haemolytic uremia syndrome/thrombolytic thrombocytopenic purpura, malaria, Dengue haemorrhagic fever, leishmaniasis, leprosy, toxic shock syndrome, *Streptococcal myositis,* gas gangrene, mycobacterium tuberculosis infections, mycobacterium avium intracellular infections, pneumocyetosis, pelvic inflammatory disease, orchitis/epidydimitis, legionella, lyme disease, influenza A virus infections, infections caused by Epstein-Barr virus, viral associated haemaphagocytic syndrome, and viral encephalitis/aseptic meningitis.

5. The method according to claim 1, wherein said treatment is for tumor therapy, in conjunction with chemotherapy, radiotherapy or cytokine administration, and wherein said tumor is at least one selected from the group consisting of of sarcomas, carcinomas, leukemias, ALL, AML, CML, CLL, small cell and non-small cell bronchial carcinoma, breast cancer, squamous cell carcinoma, Hodgkin's disease, non-Hodgkin's lymphoma, multiple melanoma, Kaposi's sarcoma, colorectal carcinoma, nasopharyngeal carcinoma, malignant histiocytosis and paraneoplastic syndrome/hypercalcaemia of malignancy.

6. The method according to claim 5, wherein said treatment is for tumor therapy in conjunction with administration of the cytokine TNF-α.

7. The method according to claim 1, wherein said treatment is for inhibiting neutral sphingomyelinase.

8. The method of claim 1, wherein X denotes —N—N=CHR$_1$.

9. The method of claim 8, wherein R$_1$ denotes CH$_3$—(CH$_2$)$_7$—.

10. The method of claim 1, wherein said compound is in the form of a racemic mixture.

* * * * *